United States Patent [19]

Bonse et al.

[11] Patent Number: 4,524,205
[45] Date of Patent: Jun. 18, 1985

[54] PROCESS FOR THE PREPARATION OF 1-AMINO-1,3,5-TRIAZINE-2,4(1H,3H)-DIONES

[75] Inventors: Gerhard Bonse, Cologne; Reinhard Lantzsch, Leverkusen; Henning Dörr, Bergisch-Gladbach; Wolfgang Kreiss, Cologne; Karlfried Dickoré, Wuppertal; Klaus Ditgens, Wuppertal; Eckart Kranz, Wuppertal, all of Fed. Rep. of Germany

[73] Assignee: Bayer Aktiengesellschaft, Leverkusen, Fed. Rep. of Germany

[21] Appl. No.: 544,334

[22] Filed: Oct. 21, 1983

[30] Foreign Application Priority Data

Nov. 6, 1982 [DE] Fed. Rep. of Germany ....... 3241114
Sep. 16, 1983 [DE] Fed. Rep. of Germany ....... 3333447

[51] Int. Cl.³ .................. C07D 251/26; C07D 251/38
[52] U.S. Cl. .................................... 544/223; 544/220
[58] Field of Search ................ 544/220, 221, 222, 223

[56] References Cited

U.S. PATENT DOCUMENTS 4,447,635 5/1984 Dickoré et al. ..................... 544/223

OTHER PUBLICATIONS

Morrison et al., *Organic Chemistry* (Textbook), 1973, Allyn and Bacon, Inc., Boston, p. 1044 and p. 685.
H. Ulrich et al., J. Org. Chem., vol. 29, pp. 2401–2404, (1964).
H. Ulrich et al., ibid., vol. 30, pp. 2779–2781, (1965).
H. Eilingsfeld et al., Chem. Ber., vol. 97, pp. 1232–1245, (1964).

*Primary Examiner*—Henry R. Jiles
*Assistant Examiner*—J. G. Mullins
*Attorney, Agent, or Firm*—Sprung Horn Kramer & Woods

[57] ABSTRACT

A process for the preparation of a herbicidally active 1-amino-1,3,5-triazone-2,4 (1H,3H)-dione of the formula

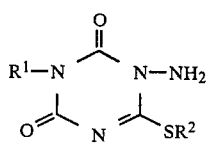
(I)

comprising in a first stage at a temperature from about 0° to 100° C. reacting an isocyanate of the formula

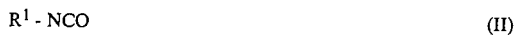
(II)

with an isothio semicarbazone of the tautomeric formulas

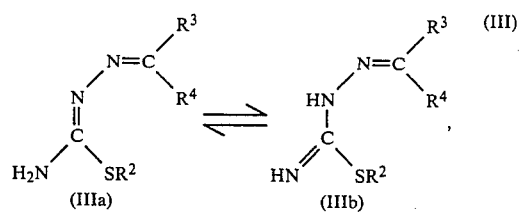

in which
R³ and R⁴ each independently is hydrogen, alkyl, cycloalkyl, aralkyl o alkyl, cycloalkyl, aralkyl or aryl, thereby to form a urea derivative of the tautomeric formulas

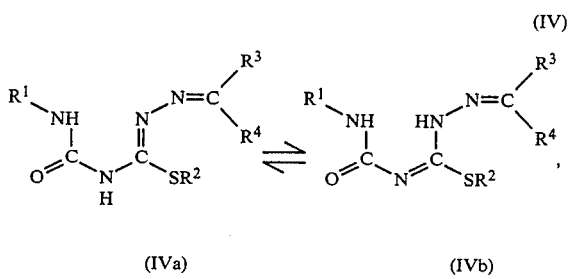

in a second stage at a temperature between about −50° and 0° C. reacting the urea derivative with phosgene (COCl₂) in the presence of an auxiliary organic base and in the presence of a diluent, at least about 2 mols of phosgene and at least about 2 mols of the auxiliary base being used per mol of urea derivative, thereby to form a 1-alkylideneamino-1,3,5-triazine-2,4(1H,3H)-dione of the formula V

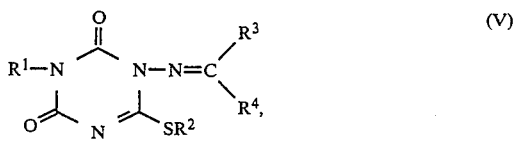

and in a third stage converting the 1-alkylideneamino group to a 1-amino group.

17 Claims, No Drawings

PROCESS FOR THE PREPARATION OF 1-AMINO-1,3,5-TRIAZINE-2,4(1H,3H)-DIONES

The present invention relates to a new process for the preparation of substantially known 1-amino-1,3,5-triazine-2,4(1H,3H)-diones, which can be used as herbicides.

It has already been disclosed that 1-amino-1,3,5-triazine-2,4(1H,3H)-diones can be prepared by reaction of N-substituted imidodicarboxylic acid dichlorides with hydrohalides of isothiosemicarbazones and subsequent acid-catalyzed hydrolysis of the 1-alkylideneamino derivatives initially formed as intermediates (compare DE-OS (German Published Specification) No. 2,254,200). However, this process has a number of disadvantages. Thus, the use of imidodicarboxylic acid dichlorides as starting substances represents considerable technical effort, since they can be prepared only by multi-stage processes (compare DE-OS (German Published Specification) No. 2,351,556) or via starting materials which are difficult to obtain (compare DE-OS (German Published Specification) No. 1,298,095), and also the yields are unsatisfactory.

It has furthermore been disclosed that 1-amino-1,3,5-triazine-2,4(1H,3H)-diones are obtained by reacting N-substituted imido-dicarboxylic acid diaryl esters with isothiosemicarbazones and hydrolyzing the 1-alkylideneamino derivatives, which are again first formed, according to the process mentioned first (compare DE-OS (German Published Specification) No. 3,006,263/EP-A2 0,034,751). However, this process can be carried out on a relatively large scale only with considerable technical effort, since the imido-dicarboxylic acid diaryl esters required as starting substances must first be prepared in a prior reaction stage by means of a high temperature reaction—by reacting carbamic acid aryl esters or primary amines with carbonic acid aryl ester-chlorides, HCl being split off, at temperatures between 100° and 300° C., preferably between about 170° and 250° C. (compare DE-OS (German Published Specification) No. 3,006,226/EP-A2 0,034,750; DE-OS (German Published Specification) No. 3,035,392/EP-A 0,048,376 and DE-OS (German Published Specification) No. 3,035,393/EP-A1 0,048,377). The high reaction temperatures require a high consumption of energy, but, in particular, considerable corrosion problems occur as a result of the hydrogen chloride liberated at the high temperatures. Moreover, the cyclization stage also requires higher temperatures (preferably about 100° C.).

In two other known processes, it is possible to react either N-chlorocarbonyl-carbamic acid O-aryl esters (compare DE-OS (German Published Specification) No. 3,106,724/EP-A1 0,058,895) or 1-cyano-N-aryloxycarbonylformamides (compare U.S. Ser. No. 346,341, filed 2/5/82, now pending, instead of the abovementioned N-substituted imidodicarboxylic acid dichlorides or diaryl esters, with isothiosemicarbazides, in order finally to obtain the same end products.

All the processes already known have the disadvantage that their realization on a large industrial scale appears uneconomical for reasons of costs, and in any case would be possible only with quite considerable capital expenditure, since the processes are multi-stage processes and some of the individual stages proceed with only unsatisfactory yields, and since the safe and inexpensive handling of the by-products unavoidably formed (hydrogen chloride at high temperatures, phenol or hydrocyanic acid) presents additional difficulties.

For the reasons mentioned, there was an urgent industrial need for an economical, technically simpler preparation process which leads to the desired group of substances.

It has now been found, surprisingly, that the 1-amino-1,3,5-triazin-2,4(1H,3H)-diones of the general formula I

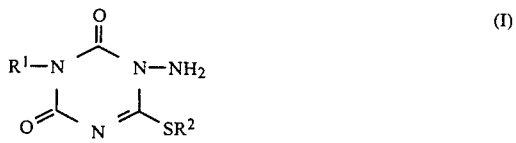

in which
R$^1$ represents an aliphatic or cycloaliphatic hydrocarbon radical or an araliphatic hydrocarbon or aryl radical and
R$^2$ represents an aliphatic hydrocarbon radical, are obtained in high yields and in a pure form by a process in which isocyanates of the general formula II

in which R$^1$ has the abovementioned meaning, are reacted with an isothiosemicarbazone of the general formula III (which can exist and react in the following tautomeric forms):

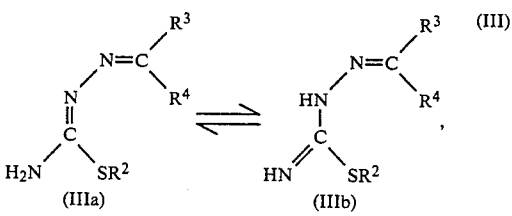

wherein
R$^2$ has the abovementioned meaning and
R$^3$ and R$^4$ are identical or different and each represents hydrogen, alkyl, cycloalkyl, aralkyl or aryl,
if appropriate in the presence of a diluent and if appropriate in the presence of a catalyst at temperatures between 0° and 100° C. (1st stage), and the new urea derivatives of the general formula IV thereby formed (which can exist and react in the following tautomeric forms):

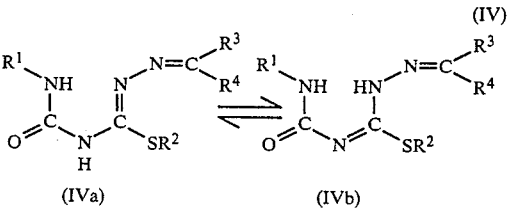

wherein R$^1$, R$^2$, R$^3$ and R$^4$ have the abovementioned meaning,
are reacted with phosgene (COCl$_2$) in the presence of an organic base and in the presence of a diluent at temperatures between −50° and 0° C., at least 2 mols of phosgene and at least 2 mols of the organic base being used per mol or urea derivatives (IV) (2nd stage), and, to remove the alkylidene protective group, if appropriate without intermediate isolation, the 1-alkylideneamino-1,3,5-triazine-2,4(1H,3H)-diones of the general formula V thereby formed, some of which are new,

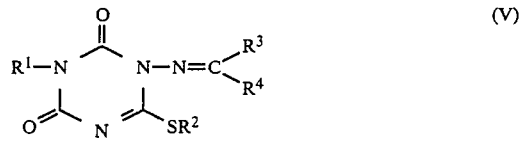

in which $R^1$, $R^2$, $R^3$ and $R^4$ have the abovementioned meaning,
are either hydrolyzed in an acid medium in a manner which is in itself known, or reacted with S-alkyl-isothiosemicarbazides or hydrohalides or monoalkyl-sulphates thereof, of the formula VI

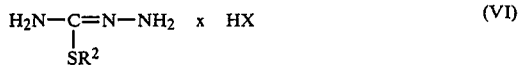

wherein
X represents chlorine, bromine or the monoalkyl-sulphate radical $R^2OSO_3$— and
$R^2$ has the abovementioned meaning,
if appropriate in the presence of a diluent and if appropriate in the presence of a catalyst at temperatures between 0° and 100° C. (3rd stage), in which case, in addition to the compounds of the formula (I)—after conversion of the hydrohalides or monoalkyl-sulphates initially formed into the free bases—the isothiosemicarbazones of the formula (III) are obtained, and can be used again in the 1st stage of the process.

The process according to the invention is distinguished by a surprisingly uniform course of reaction and thus leads—under mild conditions—to high yields of the desired end products. Especially in the second stage of the process (cyclization reaction), it would have been expected that the polyfunctional intermediates (IV) would react with phosgene in the most diverse directions, equivalent to a non-uniform course of reaction and low to infinitely small yields of the desired end products. However, even in the first process stage (addition of isocyanate onto isothiosemicarbazones) it was in no way possible to exclude from the beginning the fact that, in addition to the urea derivatives (IV) required for this synthesis route, a considerable amount of undesirable by-products would be formed. In fact, the reaction conditions discovered are of decisive importance for a successful synthesis.

The substantially improved profitability in comparison with the processes already known is a decisive industrial advantage of the new process, since in the new process the principle of building up the desired end products from very small synthesis components which is to be aimed for is realized, and the disadvantages of the known processes are avoided.

If, for example, neopentyl isocyanate and benzaldehyde S-ethyl-isothiosemicarbazone are used as starting substances, pyridine is used as the organic base in the second stage and S-ethyl-isothiosemicarbazide monoethyl-sulphate is used for variant (b) in the third stage, the course of the reaction can be represented by the following equation:

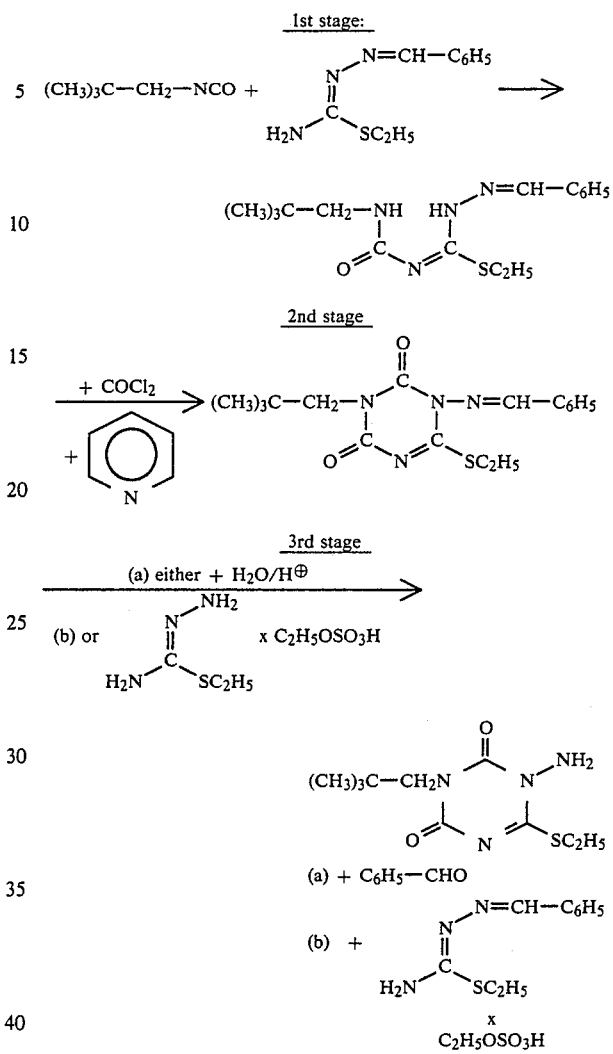

Formula (II) provides a general definition of the isocyanates to be used as starting substances. In this formula, $R^1$ preferably represents a straight-chain or branched alkyl radical with 1–12 C atoms, but excluding those alkyl radicals which carry tertiary branching on atom $C^1$ (such as, for example, tert.-butyl); or a cycloalkyl radical with 5–8 ring C atoms, excluding those radicals which are, for example, alkyl-substituted on ring atom $C^1$ (such as, for example, 1-methylcyclohexyl); or benzyl or phenyl.

The isocyanates of the formula (II) are known, or they can be prepared by known processes (compare, for example, Houben-Weyl, Methoden der Organischen Chemie (Methods of Organic Chemistry), 4th edition, Volume 8, page 119 et seq., Georg Thieme Verlag, Stuttgart, 1952).

Specific examples which may be mentioned of isocyanates of the formula (II) which can be used according to the invention are: methyl, ethyl, propyl, isopropyl, sec.-butyl, isobutyl, pentyl, isopentyl, neopentyl, 1-ethylpropyl, 1,2,2-trimethylpropyl, cyclopropylmethyl, cyclopentylmethyl, cyclohexylmethyl, (2,5-methanocyclohexyl)-methyl, cycloheptylmethyl, 2-methylpentyl, 2-ethylpentyl, 2-methylhexyl, 2-ethylhexyl, cyclopentyl, cyclohexyl, 2-methylcyclohexyl, benzyl and phenyl isocyanate.

Formula (III) provides a general definition of the isothiosemicarbazones also to be used as starting substances. In this formula, $R^2$ preferably represents a straight-chain or branched alkyl radical with 1-6 C atoms.

The radicals $R^3$ and $R^4$ can be identical or different, and in formula (III) preferably each represents hydrogen, alkyl with 1-4 C atoms, cycloalkyl with 5-7 C atoms, benzyl or an aryl radical with 6-10 C atoms. $R^3$ and $R^4$ can furthermore preferably, together with the alkylidene-C atom, form a 5-membered to 7-membered carbocyclic ring. Particularly preferably, $R^3$ represents hydrogen and $R^4$ represents phenyl or t-butyl.

The isothiosemicarbazones of the formula (III) are known, or they can be prepared by known methods, for example by S-alkylation of the corresponding thiosemicarbazones (compare Houben-Weyl, Methoden der Organischen Chemie (Methods of Organic Chemistry), 4th edition, Volume 9, page 912). The following specific isothiosemicarbazones are known:

TABLE 1

| No. | $R^2$ | $R^3$ | $R^4$ | Literature |
|---|---|---|---|---|
| (1) | —$C_2H_5$ | —H |  | Canad. J. Chem. 53, 610 (1975) |
| (2) | —$CH_3$ | —$CH_3$ |  | Chem. Soc. 1950, 452 |
| (3) | —$CH_3$ | —H |  | Canad. J. Chem. 53, 610 (1975) |
| (4) | —$CH_2$- | —H |  | Canad. J. Chem. 53, 610 (1975) |
| (5) | —$CH_3$ | —H | —$C_3H_7$ | Canad. J. Chem. 53, 610 (1975) |
| (6) | —$CH_3$ | —$CH_3$ | —$CH_3$ | Canad. J. Chem. 53, 610 (1975) |
| (7) | —$CH_3$ | | = | Canad. J. Chem. 53, 610 (1975) |
| (8) | —$CH_3$ | —H | —$C_2H_5$ | Bull. Soc. Chim. (Japan) 51, 1846 (1978) |
| (9) | —$CH_3$ | —H |  | Bull. Soc. Chim. (Japan) 54, 1767 (1981) |
| (10) | —$CH_3$ |  |  | Bull. Soc. Chim. (Japan) 54, 1767 (1981) |

Suitable diluents for the first stage of the process are all the solvents which are inert under the reaction conditions and are of industrial interest. These include hydrocarbons, such as, for example, benzene, toluene and the xylenes, chlorohydrocarbons, such as, for example, chlorobenzene; ethers, such as, for example, di-n-butyl ether, esters, such as, for example, ethyl acetate, and ketones, such as, for example, methyl isopropyl ketone; the reaction can also be carried out in water. Hydrocarbons are preferably used as the diluent, and toluene is particularly preferred.

The catalysts customary in isocyanate reactions, for example tertiary amines, such as pyridine or triethylamine, can be used as the catalyst in this stage of the process; dibutyl-tin dilaurate is preferably used.

The first stage of the process is carried out at temperatures between 0° and 100° C., preferably between 20° and 60° C. The reaction times are in general between 0.5 and 24 hours, in particular between 1 and 8 hours.

In carrying out the first stage of the process, the starting substances of the formulae (II) and (III) are preferably employed in equimolar amounts. The procedure advantageously followed is to introduce the isocyanate (II) into a solution of the isothiosemicarbazone (III) and, when the reaction had ended, the isolate the urea derivatives (IV) formed by stripping off the solvent; the yields of the urea derivatives thus obtained are between 85 and 95% of theory.

The urea derivatives (IV) which can be prepared according to stage 1 of the process according to the invention are new. If desired, they can be further purified in the customary manner, for example by recrystallization; however, they can in all cases be used directly, without further purification, in stage 2 of the process according to the invention.

Possible diluents for the second stage of the process are certain organic solvents. Suitable solvents are methylene chloride, 1,2-dichloroethane, chloroform, toluene, the xylenes, chlorobenzene, ethyl acetate, butyl acetate, acetonitrile and mixtures of these solvents. Methylene chloride and toluene are particularly preferred solvents.

The second stage of the process is carried out in the presence of an organic base (called an auxiliary base in the following text). Particularly suitable auxiliary bases are pyridine and certain substituted pyridines, possible substituents being halogen atoms and/or lower alkyl radicals. It is also possible to use other tertiary amines, such as, for example, dimethylbenzylamine. The use of pyridine as the auxiliary base is particularly advantageous.

In the second stage of the process, the reaction temperature must be between 0° and —50° C., preferably between —10° and —30° C. The reaction is most advantageously carried out under normal pressure. It proceeds rapidly and has virtually ended when the components of the reaction have been brought together.

In carrying out the second stage of the process, at least 2 mols of phosgene and at least 2 mols of the auxiliary base are employed per mol of urea derivative (IV). If smaller amounts of phosgene and auxiliary base, for example only equimolar amounts, are used, a significant reduction in yield occurs. In general, 2–10 mols of phosgene and 2–10 mols of the auxiliary base, preferably 2–4 mols of phosgene and 2–4 mols of the auxiliary base, are employed per mol of urea derivative (IV). The most favorable molar ratio of phosgene to auxiliary base is always 1:1. This means that, in carrying out process stage 2, it is particularly advantageous to react the urea derivatives (IV), phosgene and the auxiliary base in a molar ratio of 1:2:2 to 1:4:4.

The most advantageous procedure for carrying out the second stage of the process according to the invention is to take a solution of phosgene in the chosen solvent and to add the auxiliary base, if appropriate dissolved in the same solvent, with cooling. The urea derivative (IV) is introduced, either in solid form or as a solution or suspension in the same solvent, into the suspension thus obtained, also with cooling.

However, without losses in yielding occurring, a procedure can also be followed in which either the auxiliary base and the urea derivative (IV) are introduced together and simultaneously into the phosgene solution, or a solution of the auxiliary base and the urea derivative (IV) is taken and the phosgene is introduced therein, or only the urea derivative (IV) is taken and the phosgene and the auxiliary base are introduced together and simultaneously.

In the discontinuous procedure described here, the working up procedure can be the same in all cases: after a subsequent stirring time of about 30 minutes, the reaction mixture is brought to room temperature and is introduced into water, with vigorous stirring. After a further 15-minute subsequent stirring period, the organic phase is separated off and washed with water. The organic solvent is removed in vacuo, and in most cases an oily residue remains, which solidifies as crystals after being stirred with a little petroleum ether and gives the 1-alkylidene-amino-1,3,5-triazane-2,4(1H,3H)-diones of the formula (V) in yields of about 80–90% of theory.

Since the cyclization reaction (IV)→(V) proceeds at a sufficiently high rate, in a particular embodiment, the second stage of the process can also be carried out as a continuous process.

The third stage of the process serves to remove the alkylidene protective group, or to liberate the amino group in the 1-position of the triazine ring.

For this, the intermediates of the formula (V) can be hydrolyzed—if appropriate without intermediate isolation—in an acid medium in a manner which is in itself known (compare, for example DE-OS (German Published Specification) No. 2,254,200; U.S. Pat. No. 4,056,527; and European Pat. No. A2 0,034,751).

For this purpose, it is particularly advantageous to dissolve the intermediate (V) in an alcohol, such as, for example, isopropanol, to add a mineral acid, such as sulphuric acid, or an organic sulphonic acid, such as p-toluenesulphonic acid, at temperatures between about 40° and 70° C., if appropriate under reduced pressure, and to distil off from the reaction mixture the resulting carbonyl compounds of the formula $R^3—CO—R^4$, together with some of the alcohol used as the diluent. The end products (I) are isolated in a known manner by crystallization and filtration; the end products can easily be recrystallized for further purification.

However, according to the present invention, it is also possible—and in the case of an industrial procedure particularly advantageous—to transfer the protective group to isothiosemicarbazide derivatives of the above-mentioned formula (VI). Suitable diluents for this reaction are all the inert organic solvents, in particular hydrocarbons, such as, for example toluene. p-Toluenesulphonic acid has proved to be a particularly suitable acid catalyst. The reaction temperatures are in general between 0° and 100°, preferably between 20° and 80° C. The reactants (V) and (VI) are preferably employed in approximately equimolar amounts. The isothiosemicarbazide derivatives (VI) required for splitting off the protective group are known from the literature in some cases (compare, for example, Chem. Soc. 1927, page 2530 et seq.), or they can be prepared by known methods (compare the examples section).

The isothiosemicarbazones (III) obtained by this process variant are very readily soluble in non-polar solvents, after the salts initially formed have been converted into the free bases, whereas the triazine diones having the structure (I) can be filtered off and isolated, because of their low solubility in these solvents. The isothiosemicarbazones (III) which remain in the filtrate can then be used again in process stage 1 without intermediate isolation.

On further investigation into the second stage of the process according to the invention it was moreover found that by reacting pyridine with an equimolar amount of phosgene in an inert diluent, for example in methylene chloride, at temperatures between about −50° and +20° C., preferably between −30° and 0° C., not only a 1:1 adduct, but the salt-like compound defined, that is to say N-chlorocarbonyl-pyridinium chloride, of the formula VII

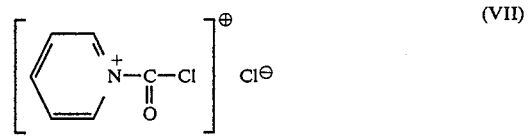

is formed. The compound (VII) can be isolated and used as such in process stage 2. Compound VII is new and is also a subject of the present invention.

The 1-amino-1,3,5-triazine-2,4(1H,3H)-diones (I) which can be prepared according to the invention are known in most cases, and they have excellent herbicidal properties (compare, for example, DE-OS (German Published Specification) 2,254,200; U.S. Pat. No. 4,056,527; and also Danish Pat. No. 136,067 and European Pat. No. A2 0,034,751).

The preparation examples which follow serve for further illustration of the invention.

EXAMPLE 1

Stage 1:

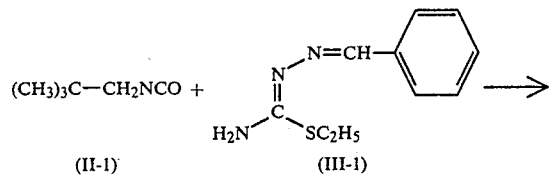

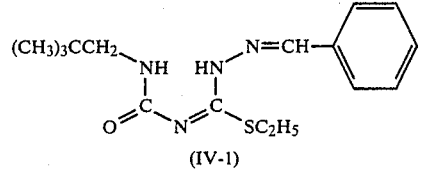

169.5 g (1.5 mols) of neopentyl isocyanate are introduced into a solution of 310.5 g (1.5 mols) of benzaldehyde S-ethyl-isothiosemicarbazone (III-1) in 2 liters of toluene. The mixture is stirred at 50° C. for 6 hours and cooled to room temperature and the urea derivative (IV-1) which has precipitated is filtered off with suction. Further pure product of melting point 140°–141° C. is obtained by concentrating the mother liquor. Yield: 451.2 g (≙94% of theory).

Stage 2:

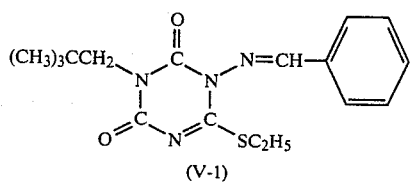

59.4 g (0.6 mol) of phosgene are introduced into 230 g of methylene chloride at +10° C. 47.5 g (0.6 mol) of pyridine, dissolved in 100 ml of methylene chloride, are then added at −20° C., with cooling. 64.0 g (0.2 mol) of urea derivative (IV-1), dissolved in 160 ml of methylene chloride, are introduced into the resulting suspension at −20° C. After a subsequent stirring period of 30 minutes, the reaction mixture is brought to room temperature and is poured into 300 ml of water, with vigorous stirring. After a further subsequent stirring period of 15 minutes, the organic phase is separated off and washed with 100 ml of water and the methylene chloride is removed in vacuo. A yellowish oil, which solidifies as crystals after being stirred with a little petroleum ether, remains. Yield: 62.4 g (≙90% of theory) of 1-benzylideneamino-6-ethylthio-3-neopentyl-1,3,5-triazine-2,4(1H,3H)-dione (V-1) of melting point 104° C.

Stage 3/Variant a:
(Hydrolysis)

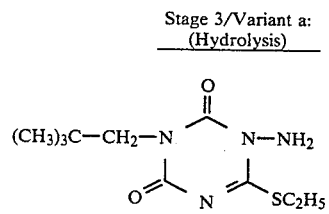

(I-1)

1.1 g of p-toluenesulphonic acid and 5.4 ml of water are added to a solution of 34.1 g (0.114 mol) of 1-isopropylideneamino-6-ethylthio-3-neopentyl-1,3,5-triazine-2,4(1H,3H)-dione (V-2) in 150 ml of isopropanol at 60° C. and the mixture is stirred at 60° C. for one hour, during which most of the reaction product crystallises out. About 80 ml of material are distilled off under 200–300 mbar, the concentrate is cooled at 0° C. and the crystals are filtered off with suction and washed with a little methanol. 26.8 g (91% of theory) of 1-amino-6-ethylthio-3-neopentyl-1,3,5-triazine-2,4(1H,3H)-dione (I-1) of melting point 202°–204° C. are obtained.

Stage 3/Variant b:

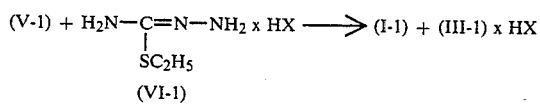

(A) X=Br⊖

5.2 g (0.015 mol) of 1-benzylideneamino-6-ethylthio-3-neopentyl-1,3,5-triazine-2,4(1H,3H)-dione (V-1), 3 g (0.015 mol) of S-ethyl-isothiosemicarbazide hydrobromide (VI-1, X=Br) and a spatula-tip of p-toluenesulphonic acid in 80 ml of toluene are stirred at 50°–55° C. for 12 hours. After the mixture has cooled, 0.6 g (0.015 mol) of sodium hydroxide in 5.4 g of water is added dropwise and the mixture is stirred at room temperature for 1 hour. The solid which has precipitated is filtered off and dried. 3.75 g (≙95% of theory) of 1-amino-6-ethylthio-3-neopentyl-1,3,5-triazine-2,4(1H,3H)-dione (I-1) of melting point 204°–205° C. are obtained.

3.0 g (≙95% of theory) of benzaledehyde S-ethyl-isothiosemicarbazone hydrobromide (III-1) are obtained as a by-product and can be re-used in stage 1.

(B) X=C₂H₅OSO₃⊖

12.25 g (0.05 mol) of S-ethyl-isothiosemicarbazide monoethyl-sulphate (VI-1, X=C₂H₅OSO₃⁻) are suspended in 80 ml of toluene. A spatula-tip of p-toluenesulphonic acid and 15.57 (0.045 mol) of 1-benzylideneamino-6-ethylthio-3-neopentyl-1,3,5-triazine-2,4(1H,3H)-dione (V-1) are added and the mixture is heated at 50° C. for 12 hours, with stirring. After cooling, 2 g (0.05 mol) of sodium hydroxide in 78 ml of water are added. The insoluble constituent is filtered off with suction and dried. 11.1 g (≙95.7% of theory) of 1-amino-6-ethylthio-3-neopentyl-1,3,5-triazine-2,4(1H,3H)-dione (I-1) of melting point 204°–205° C. are obtained.

9.9 g (≙95.4% of theory) of benzaldehyde S-ethyl-isothiosemicarbazone (VI-1) are obtained as a by-product and can be re-used in stage 1.

The following new urea derivatives (IV) can be prepared analogously to Example 1/Stage 1:

TABLE 2

$$\underset{\text{(IVa)}}{R^1\text{—NH—C(=O)—N(H)—C(SR^2)=N—N=CR^3R^4}} \rightleftharpoons \underset{\text{(IVb)}}{R^1\text{—NH—C(=O)—N=C(SR^2)—NH—N=CR^3R^4}}$$
(IV)

| Example No. | R¹ | R² | R³ | R⁴ | Melting point (°C.) |
|---|---|---|---|---|---|
| IV-2 | —⟨H⟩ | —C₂H₅ | —H | —⟨◯⟩ | 134 |
| IV-3 | —⟨H⟩ | —C₂H₅ | —CH₃ | —CH₃ | 131 |
| IV-4 | —⟨◯⟩ | —C₂H₅ | —H | —⟨◯⟩ | 142 |
| IV-5 | —⟨◯⟩ | —C₂H₅ | —CH₃ | —CH₃ | 121 |
| IV-6 | —C(CH₃)₃ | —C₂H₅ | —H | —⟨◯⟩ | 154 |
| IV-7 | —C(CH₃)₃ | —C₂H₅ | —CH₃ | —CH₃ | 120 |
| IV-8 | —CH₃ | —C₂H₅ | —CH₃ | —CH₃ | 133 |
| IV-9 | —CH₃ | —CH₃ | —CH₃ | —CH₃ | 144 |
| IV-10 | —C₃H₇—i | —C₂H₅ | —CH₃ | —CH₃ | 137 |
| IV-11 | —C₃H₇—i | —C₂H₅ | | =⟨H⟩ | 139 |
| IV-12 | —CH₂C(CH₃)₃ | —C₂H₅ | | =⟨H⟩ | 115 |

TABLE 2-continued

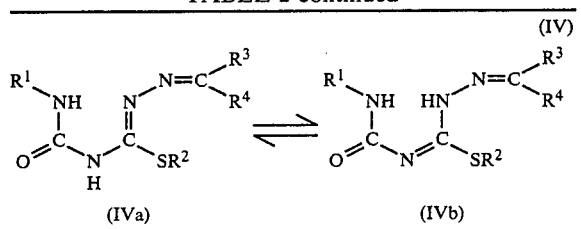

(IV) ⇌ (IVa) (IVb)

| Example No. | R¹ | R² | R³ | R⁴ | Melting point (°C.) |
|---|---|---|---|---|---|
| IV-13 | $-CH_2C(CH_3)_3$ | $-C_2H_5$ | $-H$ | phenyl | 148 |
| IV-14 | $-CH_2C(CH_3)_3$ | $-C_2H_5$ | $-H$ | $-C(CH_3)_3$ | 150 |
| IV-15 | $-CH_2C(CH_3)_3$ | $-C_2H_5$ | $-H$ | $-C_3H_7-i$ | 107 |
| IV-16 | $-CH_2C(CH_3)_3$ | $-C_2H_5$ | $-CH_3$ | phenyl | 152 |
| IV-17 | $-CH-C(CH_3)_3$ \| $CH_3$ | $-C_2H_5$ | $-H$ | phenyl | 141 |
| IV-18 | $-C_3H_7-i$ | $-CH_3$ | $-CH_3$ | $-CH_3$ | 125 |
| IV-19 | cyclohexyl | $-CH_3$ | $-CH_3$ | $-CH_3$ | 128 |

TABLE 2-continued

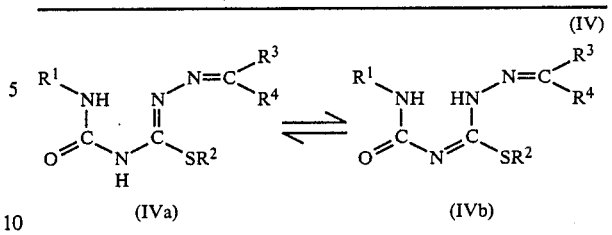

(IV) ⇌ (IVa) (IVb)

| Example No. | R¹ | R² | R³ | R⁴ | Melting point (°C.) |
|---|---|---|---|---|---|
| IV-20 | cyclopentyl | $-CH_3$ | $-CH_3$ | $-CH_3$ | 130 |
| IV-21 | $-CH_3$ | $-CH_3$ | $-H$ | phenyl | 144 |
| IV-22 | $-CH_3$ | $-CH_3$ | $-CH_3$ | phenyl | 151 |
| IV-23 | $-CH_2CH(CH_3)_2$ | $-CH_3$ | $-CH_3$ | $-CH_3$ | 148 |
| IV-24 | $-CH_2C(CH_3)_3$ | $-C_2H_5$ | $-CH_3$ | $-CH_3$ | 102 |

The following 1-alkylideneamino-1,3,5-triazine-2,4(1H,3H)-diones (V), some of which are new, can be prepared analogously to Example 1/Stage 2:

TABLE 3

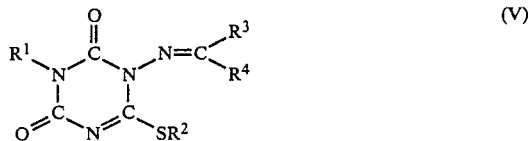

(V)

| Example No. | R¹ | R² | R³ | R⁴ | melting point (°C.) | known/new |
|---|---|---|---|---|---|---|
| V-2 | $-CH_2C(CH_3)_3$ | $-C_2H_5$ | $-CH_3$ | $-CH_3$ | 101 | known |
| V-3 | cyclohexyl | $-CH_3$ | $-CH_3$ | $-CH_3$ | 111 | known |
| V-4 | cyclopentyl | $-CH_3$ | $-CH_3$ | $-CH_3$ | 107 | known |
| V-5 | $-CH_3$ | $-CH_3$ | $-CH_3$ | $-CH_3$ | 130 | known |
| V-6 | $-CH_3$ | $-C_2H_5$ | $-CH_3$ | $-CH_3$ | 121 | known |
| V-7 | $-C_3H_7-i$ | $-CH_3$ | $-CH_3$ | $-CH_3$ | 110 | known |
| V-8 | $-CH_2C(CH_3)_3$ | $-CH_3$ | $-CH_3$ | $-CH_3$ | 122 | known |
| V-9 | $-CH_2C(CH_3)_3$ | $-C_2H_5$ | $-H$ | phenyl | 104 | new |
| V-10 | $-CH_2C(CH_3)_3$ | $-C_2H_5$ | $-H$ | $-C(CH_3)_3$ | 62 | new |
| V-11 | $-CH_2C(CH_3)_3$ | $-C_2H_5$ | phenyl | phenyl | 182 | new |
| V-12 | $-CH_2CH(CH_3)_2$ | $-CH_3$ | $-CH_3$ | $-CH_3$ | 125 | known |
| V-13 | $-CH_3$ | $-CH_3$ | $-H$ | phenyl | 94 | new |

TABLE 3-continued

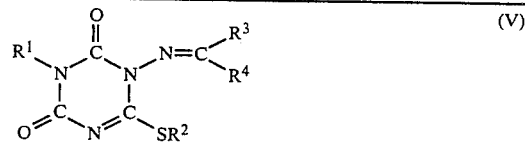

| Example No. | R$^1$ | R$^2$ | R$^3$ | R$^4$ | melting point (°C.) | known/ new |
|---|---|---|---|---|---|---|
| V-14 | —C$_3$H$_7$—i | —CH$_3$ | —H | phenyl | 90 | new |
| V-15 | cyclohexyl | —CH$_3$ | —H | phenyl | 98 | new |

The following (known) 1-amino-1,3,5-triazine-2,4-(1H,3H)-diones (I) can be prepared analogously to Example 1/Stage 3:

TABLE 4

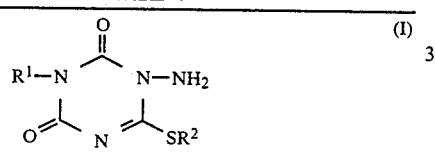

| Example No. | R$^1$ | R$^2$ | Melting point (°C.) |
|---|---|---|---|
| I-2 | cyclohexyl | —C$_2$H$_5$ | 141–142 |
| I-3 | —CH$_3$ | —C$_2$H$_5$ | 133–134 |
| I-4 | —CH$_3$ | —CH$_3$ | 174–175 |
| I-5 | —C$_3$H$_7$—i | —C$_2$H$_5$ | 147–148 |
| I-6 | —C$_3$H$_7$—i | —CH$_3$ | 148–150 |
| I-7 | cyclohexyl | —CH$_3$ | 177–179 |
| I-8 | cyclopentyl | —CH$_3$ | 158–159 |
| I-9 | —CH$_2$CH(CH$_3$)$_2$ | —CH$_3$ | 167–169 |
| I-10 | —CH$_2$C(CH$_3$)$_3$ | —CH$_3$ | 229–231 |
| I-11 | —CH$_2$—phenyl | —CH$_3$ | 127–128 |
| I-12 | —C$_4$H$_9$sec. | —CH$_3$ | 151–152 |
| I-13 | cyclohexyl | —C$_2$H$_5$ | 172–273 |
| I-14 | —C$_2$H$_5$ | —CH$_3$ | 199–201 |
| I-15 | —C$_3$H$_7$—n | —CH$_3$ | 131–132 |
| I-16 | —C$_4$H$_9$—n | —CH$_3$ | 133–134 |
| I-17 | —C$_{12}$H$_{25}$ | —CH$_3$ | 116–118 |
| I-18 | phenyl | —CH$_3$ | 205–208 |

EXAMPLE VI 1B

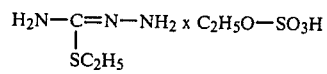

4.55 g (0.05 mol) of thiosemicarbazide, 7.7 g (0.05 mol) of diethyl sulphate and 80 ml of toluene are stirred at 80° C. for 4 hours. After the solvent has been stripped off, the salt formed, that is to say S-ethylisothiosemicarbazide monoethyl-sulphate, remains as an oil; the yield is quantitative (12.25 g).

EXAMPLE VII

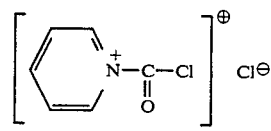 (VII)

280 g (2.83 mols) of phosgene and 224 g (2.83 mols) of pyridine are metered synchronously into 1,600 g of methylene chloride at −10° C. in the course of 180 minutes. A fine-crystalline, pale yellow suspension results. After filtration with suction, with exclusion of moisture, 480 g (=95.5% of theory) of N-chlorocarbonyl-pyridinium chloride of decomposition point 60° C. are obtained.

IR spectrum (in CH$_2$CL$_2$): 2340, 2085, 1977, 1585, 1480, 1440 and 847 cm$^{-1}$.

It will be understood that the specification and examples are illustrative but not limitative of the present invention and that other embodiments within the spirit and scope of the invention will suggest themselves to those skilled in the art.

What is claimed is:

1. A process for the preparation of a 1-amino-1,3,5-triazine-2,4(1H,3H)-dione of the formula

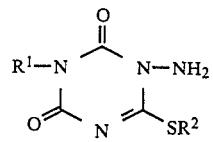

in which

R$^1$ is a C$_{1-12}$-aliphatic or a C$_{5-8}$-cycloaliphatic hydrocarbon radical or a benzyl or phenyl radical, and $R^2$ is a $C_{1-6}$-aliphatic hydrocarbon radical, comprising in a first stage at a temperature from about 0° to 100° C. reacting an isocyanate of the formula $$R^1-NCO$$

with an isothiosemicarbazone of the tautomeric formulas

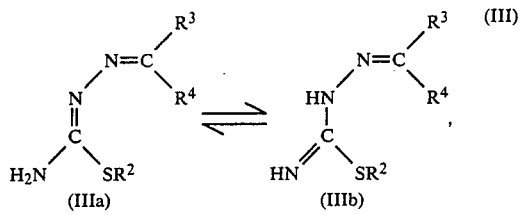

in which
$R^3$ and $R^4$ each independently is hydrogen, $C_{1-4}$-alkyl, $C_{5-7}$-cycloalkyl, benzyl or $C_{8-10}$-aryl, thereby to form a urea derivative of the tautomeric formulas

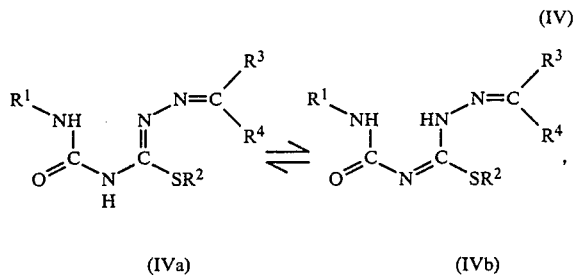

in a second stage at a temperature between about —50° and 0° C. reacting the urea derivative with phosgene ($COCl_2$) in the presence of an auxiliary organic base and in the presence of a diluent, at least about 2 mols of phosgene and at least about 2 mols of the auxiliary base being used per mol of urea derivative, thereby to form a 1-alkylideneamino-1,3,5-triazine-2,4(1H,3H)-dione of the formula V

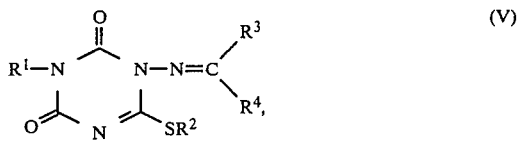

and in a third stage converting the 1-alkylideneamino group to a 1-amino group.

2. A process according to claim 1, wherein the first stage of the process is carried out at a temperature between about 20° and 60° C., the second stage of the process is carried out at a temperature between about —10° and —30° C. and the third stage of the process is carried out at a temperature between about 20° and 80° C.

3. A process according to claim 1, wherein in the second stage of the process about 2–10 mols of phosgene and about 2–10 mols of the auxiliary base are employed per mol of urea derivative.

4. A process according to claim 1 wherein in the second stage of the process, phosgene and the auxiliary base are employed in a molar ratio of about 1:1.

5. A process according to claim 1, wherein in the second stage of the process, the urea derivative (IV), phosgene and the auxiliary base are employed in a molar ratio of about 1:2:2 to 1:4:4.

6. A process according to claim 1, wherein in the first stage of the process, neopentyl isocyanate is used as the isocyanate (II) and benzaldehyde S-ethyl-isothiosemicarbazone is employed as the isothiosemicarbazone (III).

7. A process according to claim 1, wherein toluene is employed as a diluent in the first stage and methylene chloride or toluene is employed as a diluent in the second stage.

8. A process according to claim 1, wherein in the second stage of the process pyridine is employed as the auxiliary base.

9. A process according to claim 1, wherein the third stage is effected by hydrolyzing the 1-alkylideneamino compound V in an acid medium.

10. A process according to claim 1, wherein the third stage is effected by reacting the 1-alkylideneamino compound V with an S-alkyl-isothiosemi-carbazide or hydrohalide or monoalkylsulphate thereof, of the formula VI

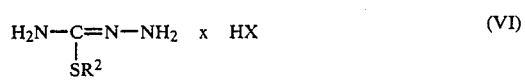

in which
X is chlorine, bromine or the monoalkyl-sulphate radical $R^2OSO_3^-$,
at a temperature between about 0° C. and 100° C. and then reacting with an alkali thereby to form the desired product along with isothiosemicarbazone of the formula (III).

11. A urea derivative of the formula

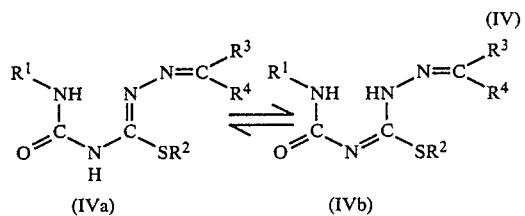

in which
$R^1$ is a $C_{1-12}$-aliphatic or a $C_{5-8}$-cycloaliphatic hydrocarbon radical or a benzyl or phenyl radical,
$R^2$ is a $C_{1-6}$-aliphatic hydrocarbon radical,
$R^3$ and $R^4$ each independently is hydrogen, $C_{1-4}$-alkyl, $C_{5-7}$-cycloalkyl, benzyl or $C_{8-10}$-aryl.

12. A urea derivative according to claim 11, in which
$R^1$ is neopentyl,
$R^2$ is ethyl,
$R^3$ is hydrogen, and
$R^4$ is phenyl.

13. A process for the preparation of a urea derivative according to claim 11, which comprises reacting an isocyanate of the formula $$R^1-NCO$$

with an isothiosemicarbazone of the tautomeric formulas

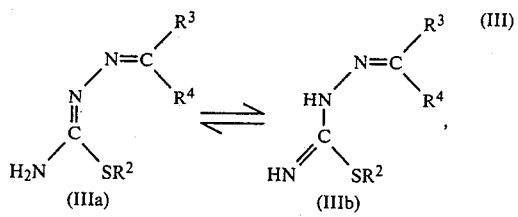

at a temperature from about 0° to 100° C.

14. A process for the preparation of a 1-amino-1,3,5-triazine-2,4(1H,3H)-dione of the formula

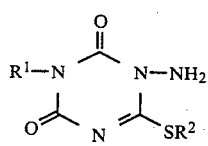

in which
R[1] is a $C_{1-12}$-aliphatic or a $C_{5-8}$-cycloaliphatic hydrocarbon radical or a benzyl or phenyl radical, and
R[2] is a $C_{1-6}$-aliphatic hydrocarbon radical, comprising reacting a 1-alkylideneamino compound of the formula

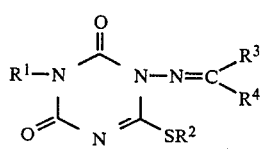

in which
R[3] and R[4] each independently is hydrogen, $C_{1-4}$-alkyl, $C_{5-7}$-cycloalkyl, benzyl or $C_{8-10}$-aryl,
with an S-alkyl-isothiosemi-carbazide or hydrohalide or mono-alkyl-sulphate thereof, of the formula VI

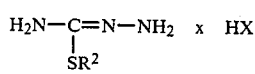

in which
X is chlorine, bromine or the monoalkyl-sulphate radical $R^2OSO_3^-$,
at a temperature between about 0° C. and 100° C. and then reacting with an alkali thereby to form the desired product along with isothiosemicarbazone of the tautomeric formulas

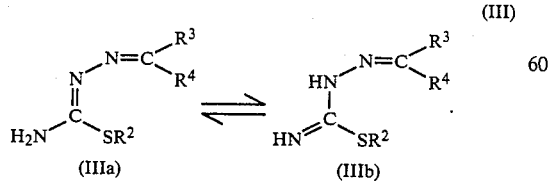

15. N-Chlorocarbonyl-pyridinium chloride of the formula

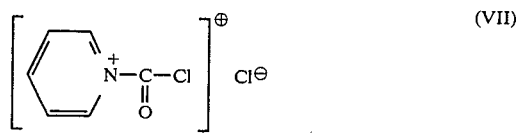

16. A process for the preparation of N-chlorocarbonyl-pyridinium chloride according to claim 15, comprising reacting pyridine with about an equimolar amount of phosgene in an inert diluent at a temperature between about −50° and +20° C.

17. A process for the preparation of a 1-alkylidene-1,3,5-triazine-2,4(1H,3H)-dione of the formula

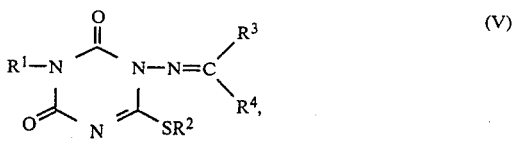

in which
R[1] is a $C_{1-12}$-aliphatic or a $C_{5-8}$-cycloaliphatic hydrocarbon radical or a benzyl or phenyl radical, and
R[2] is a $C_{1-6}$-aliphatic hydrocarbon radical, comprising in a first stage at a temperature from about 0° to 100° C. reacting an isocyanate of the formula $R^1$—NCO with an isothiosemicarbazone of the tautomeric formulas

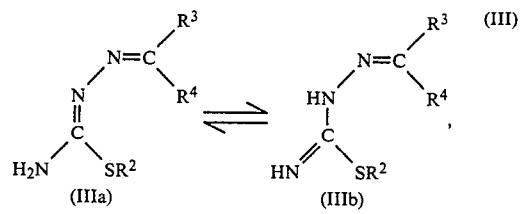

in which
R[3] and R[4] each independently is hydrogen, $C_{1-4}$-alkyl,
$C_{5-7}$-cycloalkyl, benzyl or $C_{8-10}$-aryl, which comprises reacting a urea derivative of the tautomeric formulae

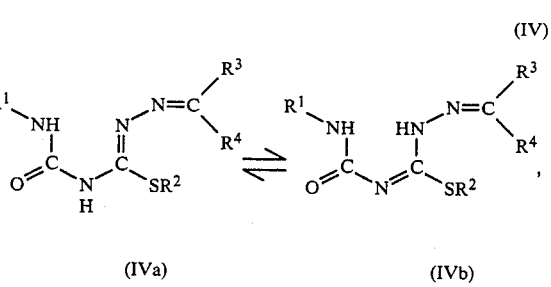

at a temperature between about −50° and 0° C. with at least about twice the molar amount of phosgene ($COCl_2$) in the presence of at least about twice the molar amount of an auxiliary organic base and in the presence of a diluent.

* * * * *